US008664596B2

(12) United States Patent
Zhao (10) Patent No.: US 8,664,596 B2
(45) Date of Patent: Mar. 4, 2014

(54) METHOD FOR CHARACTERIZING IDENTIFIED DEFECTS DURING CHARGED PARTICLE BEAM INSPECTION AND APPLICATION THEREOF

(75) Inventor: Yan Zhao, San Jose, CA (US)

(73) Assignee: Hermes Microvision, Inc., Hsinchu (TW)

(*) Notice: Subject to any disclaimer, the term of this patent is extended or adjusted under 35 U.S.C. 154(b) by 514 days.

(21) Appl. No.: 12/489,804

(22) Filed: Jun. 23, 2009

(65) Prior Publication Data
US 2010/0320381 A1    Dec. 23, 2010

(51) Int. Cl.
*H01J 37/26* (2006.01)
(52) U.S. Cl.
USPC .......................... 250/307; 250/306; 250/492.1
(58) Field of Classification Search
USPC .............. 250/306, 307, 309, 310, 311, 492.1, 250/492.2, 492.3; 430/296
See application file for complete search history.

(56) References Cited

U.S. PATENT DOCUMENTS 7,081,625 B2 * 7/2006 Furiki et al. .................. 250/310
2005/0121612 A1 * 6/2005 Okuda et al. .................. 250/311

* cited by examiner

*Primary Examiner* — Nicole Ippolito
(74) *Attorney, Agent, or Firm* — WPAT, PC; Justin King (57) ABSTRACT

A method for characterizing identified defects during charged particle beam inspection of a sample is disclosed. The method comprises obtaining a voltage contrast image of the sample by using a charged particle beam imaging apparatus at an inspection temperature; identifying, from the voltage contrast image, the presence of at least one defect on the sample; providing reference data of the sample, wherein the reference data represents at least one reference defect on the sample; comparing the location or geographical distribution of the identified defects and the reference defects on the sample to correlate the identified defects with the inspection temperature thereby characterizing the identified defects.

11 Claims, 8 Drawing Sheets

METHOD FOR CHARACTERIZING IDENTIFIED DEFECTS DURING CHARGED PARTICLE BEAM INSPECTION AND APPLICATION THEREOF

BACKGROUND OF THE INVENTION

1. Field of the Invention

The present invention relates to a method for imaging and characterizing defects on a semiconductor device which is sensitive to temperature with charged particle beam apparatus, and more particularly, to a method and apparatus for charged particle beam inspection of a semiconductor device with temperature control, and application thereof for characterizing the identified defects by separating, suppressing and/or enhancing specific defect types which are sensitive to temperature in electrical properties.

2. Background of the Related Art

Charged particle beam inspection tools are widely used in the semiconductor industry to examine physical and electrical defects in fabricated devices by observing the difference of grey level profile from the normal devices as a result of charging voltages difference induced by charged particle beam imaging. The image is also known as a voltage contrast (VC) image. For example, a normal feature is expected to be well grounded while an open circuit defect may appear relatively dark in a VC image due to excessive positive charge accumulated (positive charging is induced by scanning the interested device with charged particle beam); this is generally referred to as a dark voltage contrast (DVC) defect. On the other hand, a normal feature is expected to be floating while a short circuit or leakage defect may appear relatively bright due to excessive leakage; this is generally referred to as a bright voltage contrast (BVC) defect.

Different types of defects may appear similar voltage contrast though their generating mechanisms are different. For example, the short circuit defect and the sub-threshold leakage defect may both display as a BVC defect, but the meaning to process control and yield enhancement is totally different.

From the viewpoint of process control and yield enhancement, it is important to identify the defect types because different defects resulted from different root causes and different cures are needed. A short circuit defect is a kind of electrical defect, which is resulted from, for example, a deformed plug contacting its neighboring plug. Also, voids or keyholes formed between contact plugs/vias may lead to a shorted device. This is generally referred to as "piping". A short defect is fatal to a semiconductor device as it could cause the device inoperable. Leakage is another type of defect with strong dependency on threshold voltage (Vth) of the MOSFET devices. Intrinsic Vth varies with doping density, device dimension, thickness of gate oxide, and environmental factors such as applied voltage and temperature. Whether a leakage defect is fatal to a semiconductor device or not depends on the categories and applications of the devices.

For example, power consumption and performance of ICs are directly related to the leakage current. For low end applications, comparing to dynamic power consumption, the leakage of individual devices which are not actively changing states is often referred to as the static power consumption and is generally negligible to devices when operating. In this case, the leakage defects may be treated as nuisance defects and need to be filtered out of the short-circuit defects and other killer defects.

For high performance IC application, there has been a reduction in the supply voltage (Vdd) with the shrinking device size and thinner gate oxide. While lower Vdd corresponds to lower dynamic power consumption, it also reduces the speed of the device. In order to maintain high performances, efforts have been made to reduce the threshold voltage (Vth) of transistors. However, this encourages occurrence of the sub-threshold leakage and gate leakage. As a result, control of leakage defects in a high-end IC has become critical in current design trends for high speed devices operated at a lower threshold voltage. In particular, the varying sub-threshold voltages of devices over the entire IC being fabricated must be considered, thus there are more and more demand for not only to detect the presence of leakage defects but also to differentiate them from other types of defects, and reveal their severity.

Charged particle beam inspection tool can be used to detect the short/leakage defects as abnormal VCs, but it is often difficult to distinguish between them due to their similar VC images. Also, as mentioned earlier, there are more requirements for inspecting the leakage defect more than just determining its presence, but also for pinpointing the level of leakage.

Accordingly, it is desired to have a method to identify and distinguish between the leakage and short defects on a semiconductor device with charged particle beam apparatus, and to provide more information about the detected leakage defects so they can be characterized or categorized.

SUMMARY OF THE INVENTION

In one embodiment of the present invention, a method for characterizing identified defects during charged particle beam inspection of a sample is disclosed. The method comprises obtaining a voltage contrast image of the sample by using a charged particle beam imaging apparatus at an inspection temperature; identifying, from the voltage contrast image, presence of at least one defect on the sample; providing reference data of the sample, wherein the reference data represents at least one reference defect on the sample; comparing the location or geographical distribution of the identified defects and the reference defects on the sample to correlate the identified defects with the inspection temperature thereby characterizing the identified defects.

In another embodiment of the present invention, a charged particle beam inspection system is disclosed. The disclosed charged particle beam inspection system comprises a charged particle beam imaging apparatus, a heating/cooling apparatus, and a defect determination apparatus. The charged particle beam imaging apparatus is for forming a voltage contrast image of a sample. The heating/cooling apparatus is for changing the temperature of the sample.

The defect determination apparatus comprises a control module and an image analysis module. The control module is coupled to the charged particle beam imaging apparatus and the heating/cooling apparatus for coordinating these elements to control the temperature (the imaging temperature) of the sample when being imaged. The image analysis module is coupled with the charged particle beam imaging apparatus and the control module for receiving the voltage contrast image from the charged particle beam imaging apparatus and corresponding temperature information when imaging from the control module, so as to correlate defects of the sample identified from the voltage contrast image with the imaging temperatures, thereby characterizing the identified defects.

BRIEF DESCRIPTION OF THE DRAWINGS

FIG. 6 is a schematic diagram illustrating of an electrical failure test result of the sample in FIG. 5a.

DETAILED DESCRIPTION OF THE INVENTION

Figure 1:
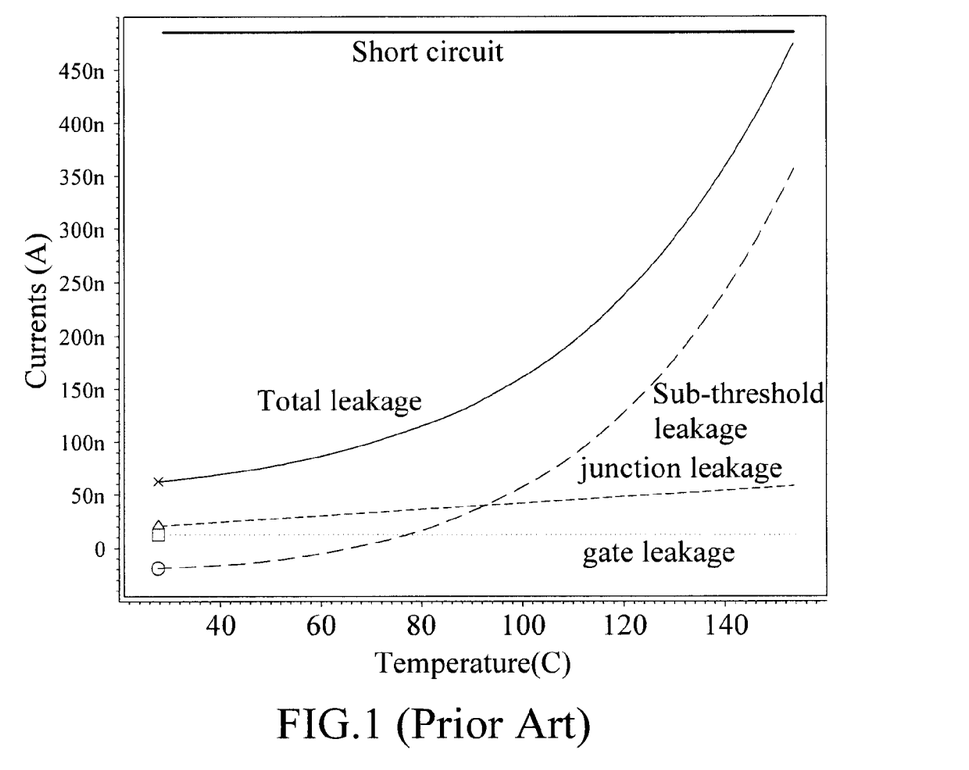
FIG. 1 is a diagram illustrating the temperature dependency of the leakage components of a typical IC device.

FIG. 1 is a diagram illustrating the temperature dependency of the leakage components of a typical IC device. As indicated, there are different mechanisms contributing to the overall leakage. The major leakage mechanism includes (1) Sub-threshold leakage, (2) gate leakage, and (3) reverse biased junction leakage. Each of these leakage components has different dependency on transistor geometry, material properties and supply voltage, and temperature. The sub-threshold leakage is a diffusion current of carrier flowing between source and drain. The sub-threshold leakage is a strong function of temperature at "off" state, that is to say, the state that supplied gate voltage is smaller than the device threshold voltage (Vgs<Vth). In MOSFET, junction leakage results from the small minority carrier diffusion/drift current across the reverse biased junction. The junction leakage is also a function of temperature. Gate leakage is mainly because electrons tunneling across the oxide as a result of the high electrical field across the thin oxide layer, so it is relatively insensitive to temperature. Illustrated in FIG. 1 is also a short-circuit type defect which serves as another example of temperature-insensitive defect. The present invention makes use of the temperature-dependency property of a semiconductor device to separate the identified temperature-sensitive defects (for example, sub-threshold leakage and junction leakage) from temperature-insensitive defects (for example, electrically short-circuit defects, and gate leakage defects) and characterize the temperature-sensitive leakage defects by grey level from voltage contrast images.

For example, a short-circuit defect is an electrical defect due to physical contact, hence its grey level generally does not vary with temperature, as illustrated in FIG. 1. For a sub-threshold or junction leakage defect, as it results from the diffusion/drift of charge carrier, the strength or even occurrence of these leakage currents could be affected by the temperature change. Therefore, a short defect can be distinguished from the temperature-dependent sub-threshold or junction leakage defect by lowering the temperature of the detected defects and observing whether their grey level changes. A gate leakage defect is temperature-insensitive, thus will behave similarly to a short-circuit defect (If necessary, It can be further differentiated from the short-circuit defect by varying the external field strength applied on the gate). As to quantify/characterize the precision of the temperature-sensitive leakage defects (e.g. killer defects/defective device vs. none-killer defects/none defective device), the same principal applies, that is, a defective leakage current flowing across the device will exist regardless of the temperature of the device, while a non-defective leakage current is less likely to be shown on a device at a low enough temperature.

Figure 2A:
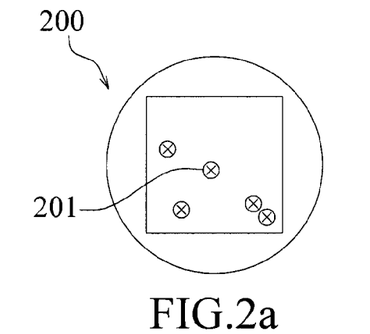
FIGS. 2a to 2d are schematic diagrams illustrating occurrence of temperature-dependent defect.
Figure 2B:
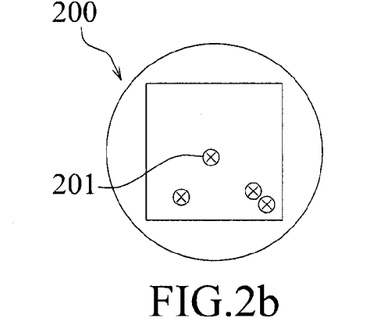
Figure 2C:
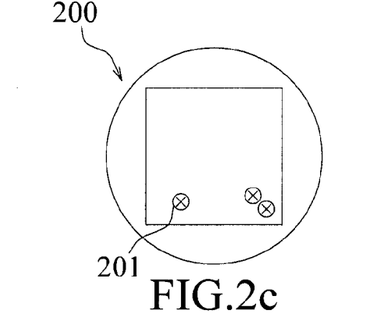
Figure 2D:
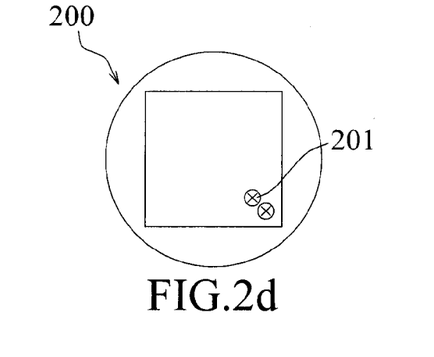

Referring to FIGS. 2a to 2d, which are schematic diagrams illustrating occurrence of temperature-dependent defect. FIG. 2a illustrates defects on a sample 200 detected by charged particle beam inspection performed at T1. Sample 200 may be a wafer. Similarly, FIG. 2b illustrates defects detected at T2, FIG. 2c illustrates defects detected at T3, and FIG. 2d illustrates defects detected at T4. Temperature T1 is higher than T2, T2 is higher than T3, and T3 is higher than T4 (T1>T2>T3>T4). As shown, at T1, five defects 201 are detected. When temperature drops to T2 and inspection is performed again, only four defects 201 are detected. As temperature keeps going down, fewer and fewer defects are detected. At T4, only two defects 201 remain observable. The number of defects detected decreases with the decreasing temperature.

This temperature-induced variation in the number of detected defects could cause inaccuracy to the inspection result, because in most cases the inspection is performed at arbitrary temperature, for example the room temperature for convenience, and thus the defects detected at the inspection temperature may not reflect the "real" defects on the sample that may affect the manufacture yield.

Accordingly, in one embodiment of the present invention, a method for characterizing identified defects during charged particle beam inspection of a sample is disclosed. The sample can be a wafer. First, the sample is imaged using a charged particle beam imaging apparatus at a higher temperature and a lower temperature, respectively, and VC images of the sample at respective temperatures are obtained. Defects on the sample are identified from respective images, and the locations of these identified defects on the sample are recorded. In one example, this location information is used to produce a defect distribution map. A defect distribution map represents the identified defects, and their location or known as geographical distribution on the sample. It is noted that the found higher and lower temperature defects could be of the same defect type with different sensitivities to temperature, or they could be different defect types or generated from different root causes, but result in substantially the same or at least similar abnormal electrical properties of the sample. For example, all short defects, junction leakage defects and sub-threshold leakage defects lead to undesired electrical connection within a device. For such case, the higher and lower temperature defects should display the same or similar grey level in the obtained grey level image, such as a bright voltage contrast (BVC).

Next, the location of the higher temperature defects on the sample is compared with the location of the lower temperature defects on the sample. If a higher temperature defect is found at the same position corresponding to lower temperature, such higher temperature defect is said to be a "common defect". In other words, the common defect is a defect which is observed at a higher temperature, and remains as an observable defect when the temperature is lowered. Higher temperature defects that do not have corresponding lower temperature defects located at the same position on the sample will be referred to as "non-common" defects hereinafter.

Therefore, in this embodiment, the lower temperature image is used as a reference for finding the above defined common defects.

In some cases, the common defect is considered to be more serious than the non-common defect, as it is more persistent by showing up even at the lower temperature. For example, if the found defects are leakage defects, then the common leakage defects should be of a higher level of leakage than the non-common ones. The non-common defects on the contrary, as they have a sensitive temperature-dependent behavior over the given temperature range, are less likely to be an issue toward operation of the interested device they are located on.

In one aspect, the purpose of finding the common defects is to correlate the higher temperature defects with the higher temperature so that temperature can become an index for characterizing the found defects.

For example, a wafer may first be inspected at a very high and a very low temperature regime. At the high temperature regime, a large quantity of defects (leakage defects plus short defects) tends to be detected. A threshold for an intolerable number of total defects can be predefined, thus at a high enough temperature the number of detected defects will reach this threshold. At the low temperature regime on the other hand, a smaller quantity of defects tends to be detected. If the imaging temperature is low enough, only temperature-insensitive defects (e.g. short defects) will show, for example, showing in the defect distribution map. The defect distribution map at such temperature can thus serve as a reference of inspection for the interested sample.

In this case, the detected temperature-insensitive defects (for example short defects) on the sample are the common defects, and the detected temperature-sensitive leakage defects (e.g. sub-threshold leakage) are the non-common defects. Therefore, the temperature-sensitive leakage defects can be filtered out when the higher temperature inspection result is interpreted with reference to the lower temperature defect distribution map.

Similarly, the lower imaging temperature can be selected so that both the temperature insensitive defects (e.g. short defects) and serious temperature-sensitive leakage defects (e.g. sub-threshold leakage) are represented in the lower temperature defect distribution map. Therefore, nuisance leakage defects can be filtered out when the higher temperature inspection result is interpreted with reference to the lower temperature defect distribution map.

In summary, when the inspection is performed at different higher temperatures, the imaging temperatures, the VC behavior of the interested sample in individual obtained grey level images reveals the abnormal electrical properties of the interested sample at corresponding imaging temperature when a lower temperature inspection result is available as a reference.

For example, the number of the temperature-insensitive defects (short defects and/or gate leakage defects) as well as the temperature-sensitive defects (sub-threshold and/or junction leakage defects) on the sample can be estimated. The two numbers combined may make the sample to be considered defective. If the number of the temperature-insensitive defects itself exceeds a tolerable threshold, the sample is considered defective. As for temperature-sensitive leakage defects, the total number of detected defects can be compared with a tolerable threshold value to determine if the inspected device is acceptable, or further analysis such as more temperature-based inspections may be performed to exclude the nuisance temperature-sensitive leakage defects.

In one embodiment, instead of the lower temperature image, an electrical failure test result of the interested devices on the sample is used as the reference. The electrical failure test is a test that can identify the defective devices on the sample based on electrical failures. The test parameters can be selected to carry out the detection of leakage defects on the sample. The electrical failure test is typically performed at the operating temperature of the interested devices on the sample. Thus, the defects indicated by the electrical failure test are the ones that will fail at the desired operational condition. In other words, they are the "real" defects. It is noted that the temperature of the electrical failure test could be higher, equal to or lower that the higher temperature at which the charged particle beam inspection is performed.

In this embodiment, again the location of the higher temperature defects are compared with the location of the electrical failure defects identified from the electrical failure test result. For example, the geographical distribution of the higher temperature defects on the sample (e.g. a wafer) is compared with the geographical distribution of electrical failure defects on the sample.

Such comparison can be a qualitative analysis, for instance, considering the shape of defect distribution over the sample. Assume the electrical failure test is set to detect sub-threshold leakage defects on a sample, and the detected defects are distributed over the sample in a certain shape. Now, if the shape of distribution of the higher temperature defects over the sample is similar to that of the detected electrical failure defects, it is determined that the inspection performed at the higher temperature substantially catches the presence of the interested defects, the sub-threshold leakage defects. Consider the sample to be a wafer, the "shape" of defect distribution can be, for example, a donut shape on the outer rim portion of the wafer, or randomly distributed on the center portion of the wafer etc.

In one example, similarity degree of the defect distribution shapes is determined arbitrarily.

In one example, a series of images, each formed at a corresponding imaging temperature, are compared with the electrical failure test result performed at a designated temperature. This designated temperature may be selected to be the operating temperature of the interested devices on the sample, for example, the room temperature. Defects on the sample are identified from respective images, and the locations of these identified defects on the sample are recorded, so that for each imaging temperature, a shape in which the identified defects are distributed over the sample is recognized. Then, these defect distribution shapes at different imaging temperatures are compared with the defect distribution shapes observed from the electrical failure test result. A most matched distribution shape of the higher temperature defects to the electrical failure defects is determined, and the corresponding imaging temperature is considered to be suitable for inspection of the interested sample.

Figure 3:
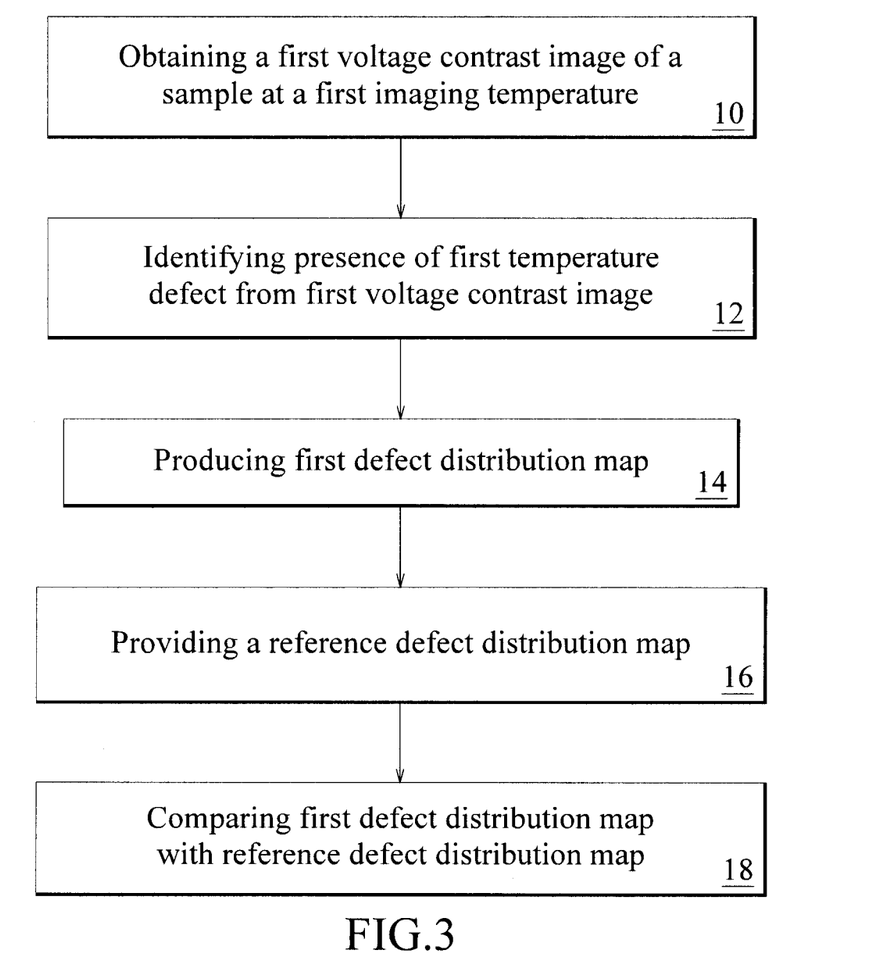
FIG. 3 is a flow chart illustrating a method for characterizing identified defects during charged particle beam inspection of a sample in accordance with an embodiment of the present invention.

FIG. 3 is a flow chart illustrating a method for characterizing identified defects during charged particle beam inspection of a sample in accordance with an embodiment of the present invention. Referring to FIG. 3, the method comprises the following steps. In step 10, a first voltage contrast image of the sample is obtained at a first imaging temperature by using a charged particle beam imaging apparatus. The first imaging temperature may be selected to be within a range of −50° C. to 350° C. In one embodiment, the first imaging temperature is selected to be room temperature.

In step 12, the presence of at least one first temperature defect on the sample is identified, for example, by observing a grey level profile of the sample displayed in the first voltage contrast image. It is noted that the purpose of step 12 is to identify detects from the first voltage contrast image; several well known approaches of image inspection can be used to carry out step 12, and the details of these approaches will not be described here to avoid unnecessary limitations on the present invention. Examples of well known image inspection approaches include die-to-die mode inspection, array mode inspection, die-to-database mode inspection, etc.

Figure 4A:
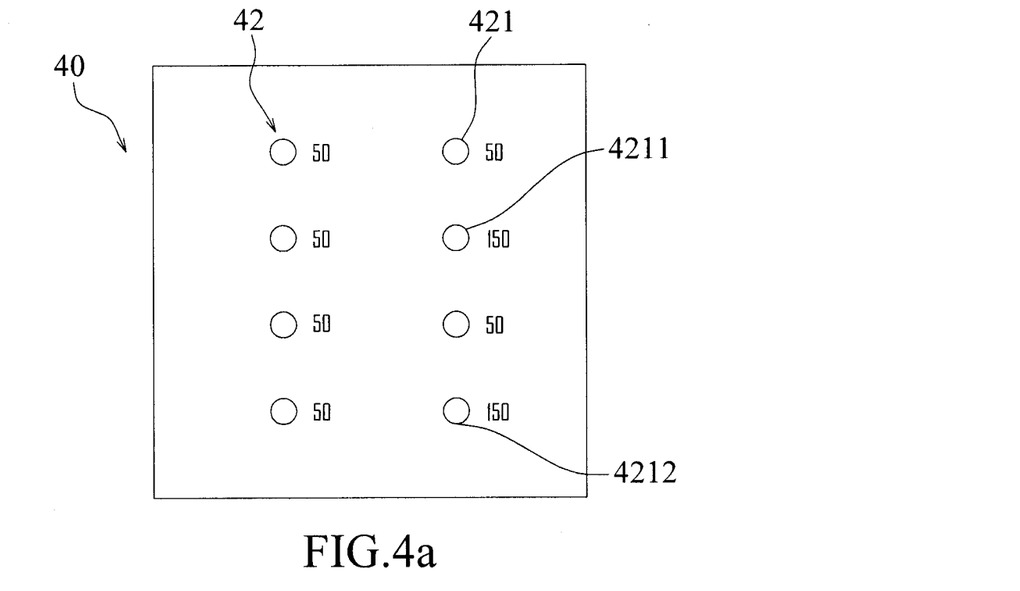
FIG. 4a to FIG. 4c are schematic diagrams illustrating execution of an inspection method by means of charged particle beam in accordance with an embodiment of the present invention.
Figure 4B:
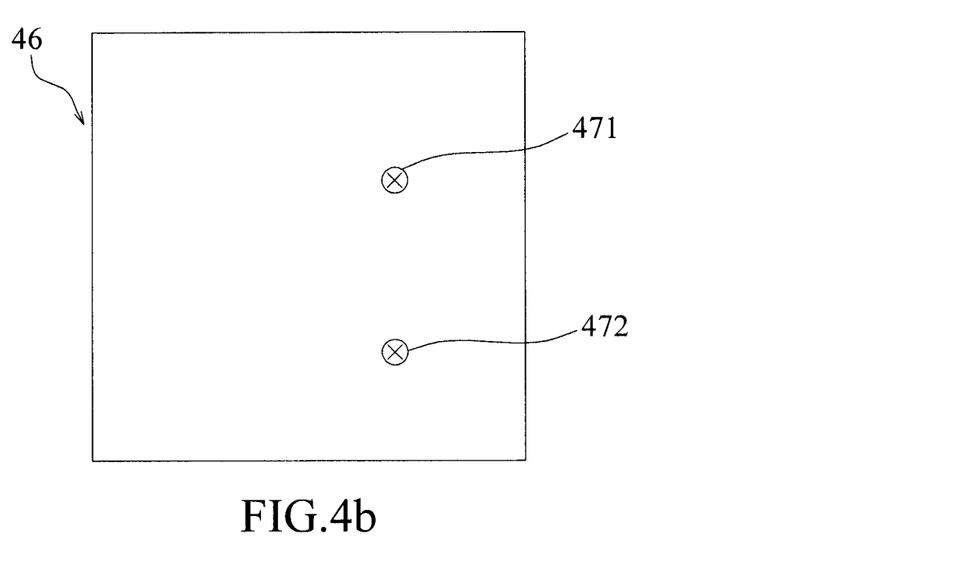

Reference is now made to FIG. 4a and FIG. 4b, which are two schematic illustrations of execution of the disclosed method in accordance with an embodiment of the present invention. FIG. 4a illustrates the above first voltage contrast image obtained from step 10. As shown in FIG. 4a, a voltage contrast image 40 comprises a grey level profile 42 displayed therewithin. In this embodiment, the grey level profile 42 includes an array of spots 421 which displays various grey levels. Spots 421 may represent, for example, conductive plugs within a semiconductor device such as contact plugs within a MOSFET device. For convenience of describing the grey level profile 42, grey level of individual spots 421 are represented in numbers, as illustrated in FIG. 4a. The higher the grey level is, the brighter the spot 421 is.

It can be seen in image 40 that the second spot 421 in the right column, denoted as 4211, and the bottom spot 421 in the same column, denoted as 4212, have a grey level extraordinarily higher than the other spots 421. In this embodiment, spot 4211 and 4212 are identified as a BVC defect from image 40, which is the first temperature defect described earlier in step 12. It is noted that it is not a necessary condition that spot 4211 and 4212 have the same grey level (150) in FIG. 4a; the grey level of spot 4211 and 4212 can be different.

Next, in step 14, the location of the identified first temperature defects is recorded and used to produce a first defect distribution map accordingly, wherein the first defect distribution map represents the identified first temperature defects and their location on the sample. In other words, the first defect distribution map represents the geographical distribution of the first temperature defects on the sample. The first defect distribution map may be generated through implementation of software.

FIG. 4b illustrates a first defect distribution map 46, which is formed from voltage contrast image 40. As illustrated in FIG. 4b, in first defect distribution map 46, two identified first temperature defects 471 and 472 from image 40 are shown.

In step 16, a reference defect distribution map is provided, wherein the reference defect distribution map represents at least one reference defect and location thereof on the sample. In other words, the reference defect distribution map represents the geographical distribution of the reference defects on the sample. In one embodiment, the reference defect distribution map is a second defect distribution map produced from a second voltage contrast image of the sample obtained from inspection performed at a second imaging temperature, wherein the second defect distribution map represents at least one second temperature defect and location (geographical distribution) thereof on the sample. The second imaging temperature may be selected to be within a range of −50° C. to 350° C. It is noted that to be the reference, the second imaging temperature is preferably selected to be lower than the first imaging temperature.

Figure 4C:
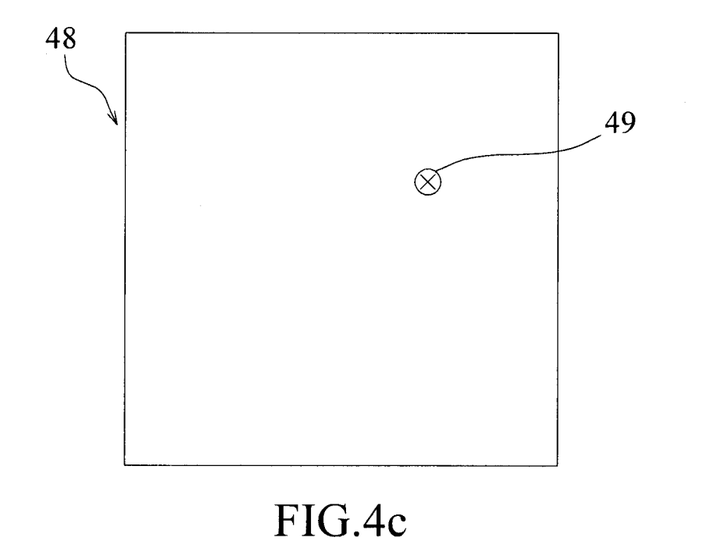

FIG. 4c illustrates a second defect distribution map 48. As illustrated in FIG. 4c, in second defect distribution map 48, one identified second temperature defect 49 is shown.

In step 18, the first defect distribution map and the reference defect distribution map are compared for characterization of the first temperature defects. For example, in this case, with the reference being selected to be a second defect distribution map, the comparison is to determine the presence of at least one of the first temperature defects which has a locationally corresponding reference defect on the sample. If such reference defect exists, the considered first temperature defect is categorized as a common defect. The rest first temperature defects on the other hand, are categorized as non-common defects.

This situation mentioned above can be seen from FIG. 4b and FIG. 4c. First temperature defect 471 in first defect distribution map 46 has a locationally corresponding second temperature defect 49 in second defect distribution map 48, while the other first temperature defect 472 does not. Therefore, in this embodiment, first temperature defect 471 will be categorized as a common defect and first temperature defect 472 will be categorized as a non-common defect.

In one embodiment, the reference defect distribution map is selected to be an electrical failure test result of the sample, and the reference defects are those determined by the electrical failure test performed. In this embodiment, the produced first defect distribution map is compared with the reference defect distribution map to see how well the shape of distribution of the first temperature defects matches the shape of distribution of the reference defects on the sample. The result is then used to help select a suitable temperature for inspection of the interested sample.

Figure 5A:
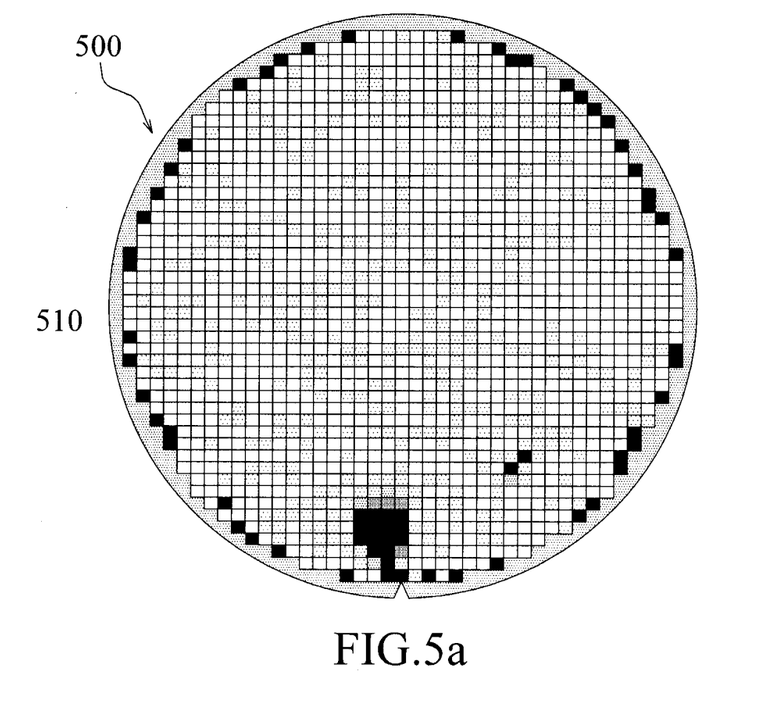
FIG. 5a to FIG. 5c are diagrams respectively illustrating a defect distribution map produced from charged particle beam inspection of a sample performed at various temperatures.
Figure 5B:
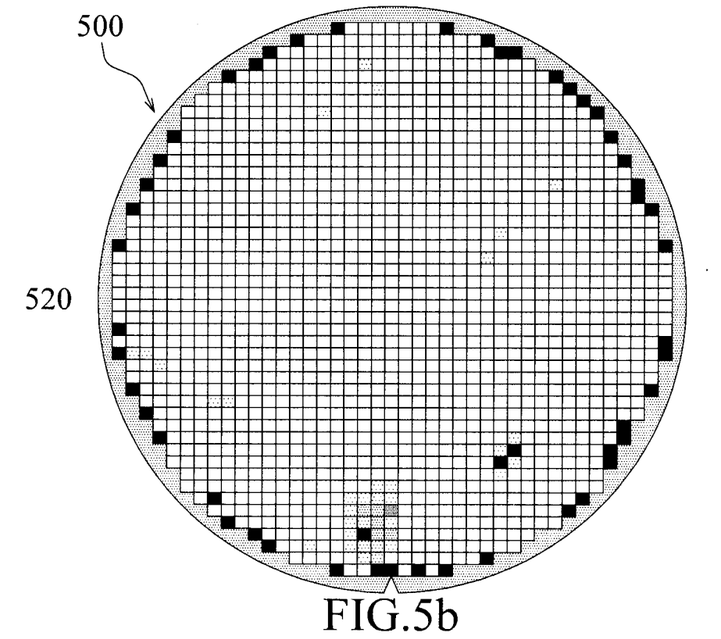
Figure 5C:
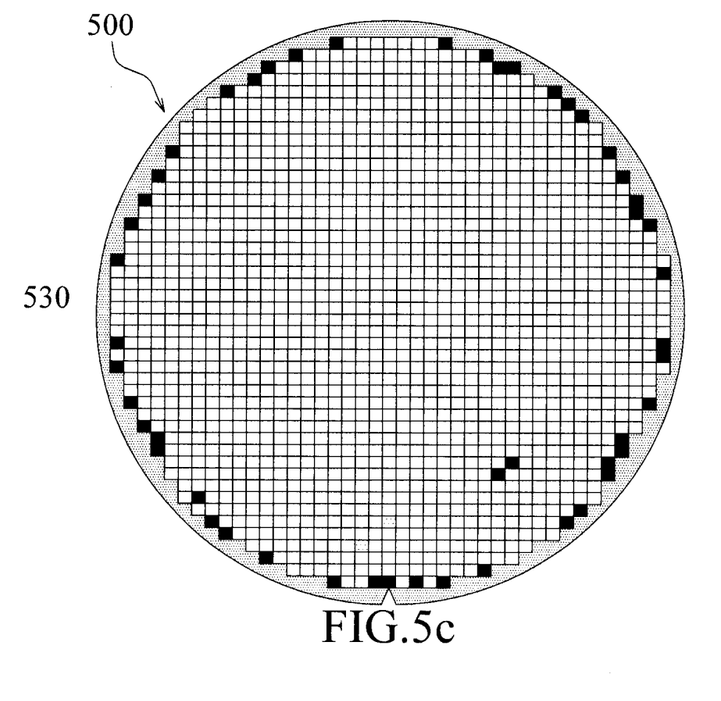

FIG. 5a to FIG. 5c are three diagrams respectively illustrating a defect distribution map 510 which is produced from charged particle beam inspection of a sample 500 performed at an imaging temperature T510, a defect distribution map 520 for an imaging temperature T520, and a defect distribution map 530 for an imaging temperature T530 in accordance with an embodiment of the present invention. Temperature T510 is higher than temperature T520, and temperature T520 is higher than temperature T530 (T510>T520>T530).

In this embodiment, sample 500 is a wafer which includes a plurality of dies formed thereon. The dies are represented in small squares, as shown in FIGS. 5a to 5c. It is noted that in this embodiment, the detected defects are represented in the form of bad dies on sample 500, wherein a bad die is defined to have a quantity of defects thereon which exceeds a preselected threshold. The bad dies are represented in the maps as dark squares. Grey squares indicate dies having relatively fewer defects and are less defective as compared to the dark black squares.

It can be seen from map 510 to map 530 that the number of detected defects decreases with temperature, but the fundamental shape of distribution of the defects, which is a donut shape, retains in all maps.

In map 510 and 520 there are a group of bad dies located on the lower portion of sample 500. As shown from FIG. 5a to FIG. 5c, the number of these bad dies decreases from map 510 (obtained at T510) to map 520 (obtained at T520 which is lower than T510). In map 530, substantially all these bad dies disappear. On the other hand, bad dies distributed on the outer rim portion of sample 500 are present in all maps. Therefore, in this case it may be inferred that the defects distributed on the outer rim portion of sample 500 are more likely to be temperature-insensitive (e.g. short or gate leakage) defects or serious temperature-sensitive (e.g. severe sub-threshold or junction leakage) defects, while the defects distributed on the lower portion of sample 500 are more likely to be less temperature-sensitive leakage defects. For example, they could be nuisance leakage defects.

Figure 6:
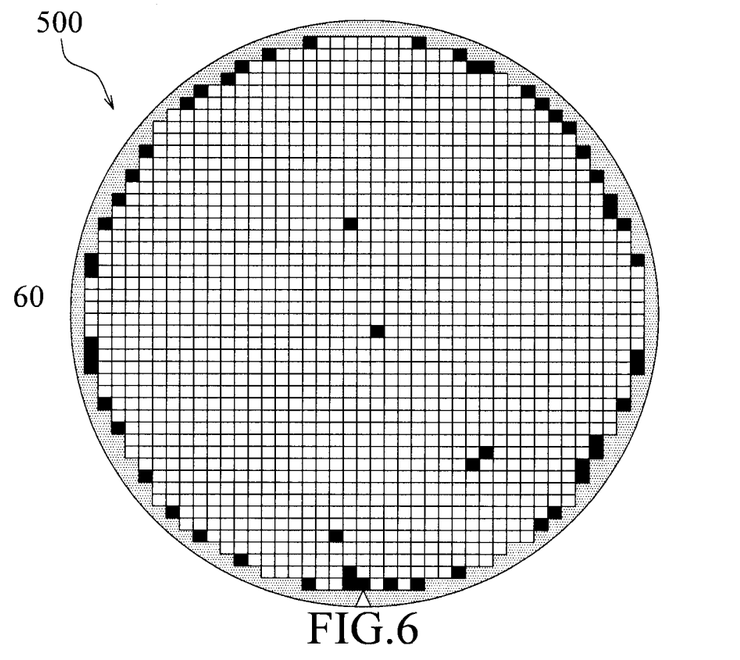

Referring to FIG. 6, which is a schematic diagram illustrating an electrical failure test result 60 of sample 500 in FIG. 5a. The electrical failure test is performed on the same sample 500 and may be selected to be performed at a predefined test temperature, for example at the room temperature or the desired operating temperature of the interested devices on sample 500. The target defect to be tested should be of the same type as that which was detected by charged particle beam inspection in the embodiment of FIG. 5. Or, the interested defect type(s) of both the test and the inspection should at least cause substantially the same abnormal electrical property to sample 500. For example, both the inspection and the test are to detect short or leakage defects that lead to undesired electrical connection within sample 500. As shown in electrical failure test result 60, the identified defects, again represented as bad dies, are distributed mostly on the outer rim region of sample 500 and form a donut shape.

The above obtained defect distribution maps 510, 520 and 530 are then compared with electrical failure test result 60. It can be seen from FIG. 5 and FIG. 6 that defect distribution map 530 best matches electrical failure test result 60 in terms of the shape of distribution of the identified defects and reference defects. Therefore, in this embodiment, T530 will be selected to be the most suitable temperature, of the three temperatures T510, T520 and T530, for inspection of sample 500.

As described above, by referencing to the defect distribution map, not only the number of the identified defects can be estimated, but also the geographical distribution of the defects on the sample can be analyzed. This can be useful in certain inspection job scenarios. For example, some areas on the sample may comprise particular type(s) of devices which is sensitive to sub-threshold leakage defects. Therefore, a proper threshold, for example the number of sub-threshold leakage defects, may be applied for determining the yield of these areas. Other determination may involve power consumption or performance requirements of the interested devices. For example, the power consumption performance of the device may be defined, whereby the limitation on the leakage current flowing across the device may be estimated.

In one sense, the present invention can be used to suppress or enhance particular defects sensitive to the temperature. For instance, the sample may be heated during or prior to the inspection to stimulate sub-threshold and/or junction leakage, so that these temperature-sensitive leakage defects can be detected. Or, the sample may be cooled during or prior to the inspection to suppress the sub-threshold and/or junction leakage, so that the temperature-insensitive defects (such as the short defect and/or the gate leakage defect) can be distinguished from the temperature-sensitive leakage defects.

Figure 7:
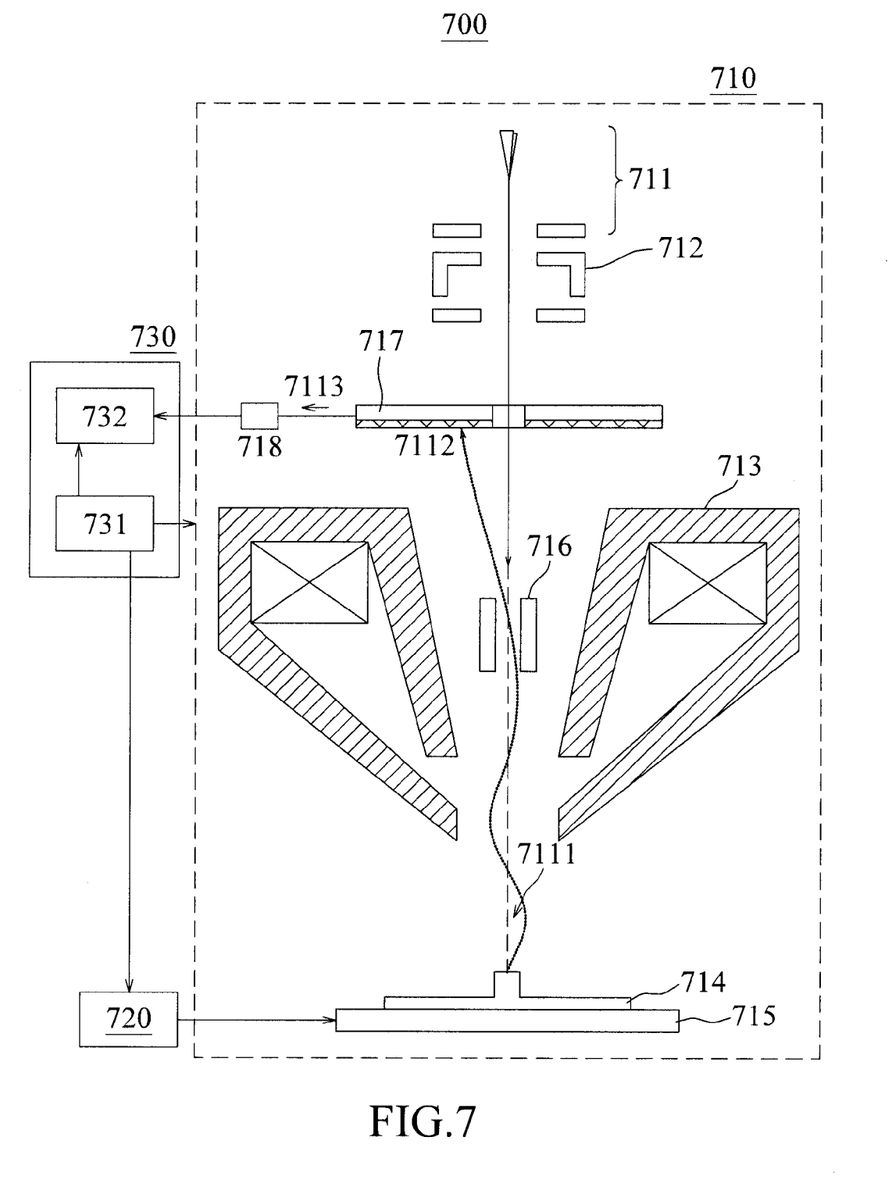
FIG. 7 is a schematic diagram of a charged particle beam inspection according to an embodiment of the present invention.

In one embodiment, a charged particle beam inspection system is disclosed. Referring to FIG. 7, which is a schematic diagram of a charged particle beam inspection system according to an embodiment of the present invention. As shown, a charged particle beam inspection system 700 comprises a charged particle beam imaging apparatus 710, a heating/cooling apparatus 720, and a defect determination apparatus 730. Charged particle beam imaging apparatus 710 is for forming a voltage contrast image of an interested sample. Heating/cooling apparatus 720 is for causing temperature change to the interested sample. Defect determination apparatus 730 comprises a control module 731 and an image analysis module 732.

Control module 731 is coupled to charged particle beam imaging apparatus 710 and heating/cooling apparatus 720 for coordinating these elements such that when the interested sample is being imaged, its temperature, which will be referred to as the imaging temperature hereinafter, is properly controlled for the purpose of characterizing the identified defects. In one example, control module 731 also collects temperature information of the interested sample from heating/cooling apparatus 720. Image analysis module 732 is coupled with charged particle beam imaging apparatus 710 and control module 731 for receiving the voltage contrast image from charged particle beam imaging apparatus 710 and corresponding temperature information of the interested sample when being imaged from control module 731, so as to correlate defects on the interested sample identified from the voltage contrast image with the corresponding imaging temperatures, thereby characterizing the identified defects.

Charged particle beam imaging apparatus 710 may be a conventional charged particle beam microscope, such as a scanning electron microscope (SEM). As shown in FIG. 7, in charged particle beam imaging apparatus 710, a charged particle beam generator 711 generates a charged particle beam, and then the charged particle beam is condensed and focused by a condenser lens module 712 and an objective lens module 713, respectively, to form a charged particle beam probe 7111. The formed charged particle beam probe 7111 then bombards the surface of a sample 714 secured on a stage 715. Charged particle beam probe 7111 is controlled by a deflection module 716 to scan the surface of sample 714. After the charged particle beam probe 7111 bombards the surface of sample 714 secondary charged particles 7112 are induced to emit from the sample surface along with other charged particles of beam probe 7111 reflected by sample 714. These particles are then detected and collected by a detector module 717. Then, detector module 717 generates a detection signal 7113 accordingly. An image forming module 718 coupled to detector module 717 receives detection signal 7113 and accordingly forms a charged particle microscopic image (grey level image) of sample 714.

In one example, heating/cooling apparatus 720 is coupled to sample stage 715, and image analysis module 732 is coupled to image forming module 718. In another example, control module 731 coordinates the relative motion of charged particle beam probe 7111 and sample 714, for instance by controlling deflection module 716 and the sample stage 715 to perform scanning of charged particle beam probe 7111 over the surface of sample 714 thereby forming image of sample 714.

With the temperature controlled, charged particle beam inspection system 700 is able to carry out the defect characterization method disclosed in embodiments as shown in FIG. 3 to FIG. 6. For example, the action of heating/cooling apparatus 720 is brought into coordination with deflection module 716 and stage 715 by control module 731 such that imaging of sample 714 at various temperatures can be carried out; defects are identified and compared with the designated reference by image analysis module 733 for characterizing the identified defects, as described above.

Although the present invention has been explained in relation to its preferred embodiment, it is to be understood that other modifications and variation can be made without departing the spirit and scope of the invention as hereafter claimed.

What is claimed is:

1. A method for characterizing defects during charged particle beam inspection of a sample, comprising:

obtaining a first voltage contrast (VC) image of said sample by using a charged particle beam imaging apparatus at a first imaging temperature from a first direction;

constructing a first defect distribution map of said sample from said first direction according to said first VC image;

obtaining a second VC image of said sample by using said charged particle beam imaging apparatus at a second imaging temperature from said first direction, wherein said second imaging temperature is different from said first imaging temperature;

constructing a second defect distribution map of said sample from said first direction according to said second VC image; and comparing said first defect distribution map with said second defect distribution map.

2. The method according to claim 1, wherein said first direction is from top of said sample to bottom of said sample.

3. The method according to claim 1, wherein said comparing said first defect distribution map with said second defect distribution map further comprises identifying common defects and non-common defects between said comparing said first defect distribution map and said second defect distribution map.

4. The method according to claim 1, wherein said comparing said first defect distribution map with said second defect distribution map further comprises identifying temperature-sensitive leakage defects and temperature-insensitive leakage defects.

5. The method according to claim 4, wherein said temperature-insensitive leakage defects comprise short circuit defects, and said temperature-sensitive leakage defect comprise sub-threshold leakage and reverse biased junction leakage.

6. The method according to claim 1, wherein said second imaging temperature is lower than said first imaging temperature.

7. The method according to claim 1, wherein said first imaging temperature is within a range of −50° C. to 350° C.

8. The method according to claim 1, wherein said first imaging temperature is room temperature.

9. A method for characterizing defects of a sample, comprising:
   conducting a reference defect test on said sample at a reference test temperature;
   constructing a reference defect distribution map of said sample from an inspecting direction according to said reference defect test;
   conducting a first defect test on said sample at a first temperature, wherein said first temperature is different from said reference test temperature;
   constructing a first defect distribution map of said sample from said inspecting direction according to said first defect test; and
   comparing said first defect distribution map with said reference defect distribution map.

10. The method according to claim 9, wherein said reference defect test is an electrical failure test for testing electrical failure defects.

11. The method according to claim 9, wherein said first defect test is a charged particle beam inspection.

* * * * *